United States Patent [19]

Meserve

[11] Patent Number: Plant 7,652

[45] Date of Patent: Sep. 17, 1991

[54] ILEX PLANT-MESGOLG VARIETY

[75] Inventor: Kathleen K. Meserve, Vero Beach, Fla.

[73] Assignee: The Conard-Pyle Company, West Grove, Pa.

[21] Appl. No.: 508,709

[22] Filed: Apr. 3, 1990

[51] Int. Cl.[5] ..... A01H 5/00

[52] U.S. Cl. ..... Plt./65

[58] Field of Search ..... Plt./65

[56] References Cited

U.S. PATENT DOCUMENTS

| | | | |
|---|---|---|---|
| P.P. 2,434 | 8/1964 | Meserve | Plt. 65 |
| P.P. 2,435 | 8/1964 | Meserve | Plt. 65 |
| P.P. 3,517 | 3/1974 | Meserve | Plt. 65 |
| P.P. 3,662 | 12/1974 | Meserve | Plt. 65 |
| P.P. 3,675 | 1/1975 | Meserve | Plt. 65 |
| P.P. 4,685 | 4/1981 | Meserve | Plt. 65 |
| P.P. 4,804 | 1/1982 | Meserve | Plt. 65 |

*Primary Examiner*—Howard J. Locker

*Attorney, Agent, or Firm*—Burns, Doane, Swecker & Mathis

[57] ABSTRACT

A new and distinct variety of *Ilex* × *meserveae* is provided which originated by crossing *Ilex aquifolium* 'Fructa Lutea' × *Ilex rugosa*. The new variety possesses attractive deep green foliage having a glossy upper surface, exhibits a dense branching pyramidal growth habit, and forms in abundance berries which when mature exhibit an attractive lemon-yellow coloration. Pistillate flowers are formed in abundance in the springtime and good tolerance to cold is exhibited in the wintertime. The new variety is particularly well suited for growing as a specimen plant which during the winter displays a striking contrast of bright yellow berries surrounded by a background of deep green foliage.

1 Drawing Sheet

SUMMARY OF THE INVENTION

The present invention relates to a new and distinct variety of *Ilex* × *meserveae* which was originated by me by crossing *Ilex aquifolium* 'Fructa Lutea' (non-patented in the United States) × *Ilex rugosa*.

The objective of my breeding was to create a hardy, upright, and more decorative shrub of the genus Ilex through the combination of the hardiness of *Ilex rugosa* and the beautiful foliage and unique yellow fruit coloration of *Ilex aquifolium* 'Fructa Lutea'. It was desired to create a new variety which is well suited to fulfill a wide range of environmental landscape needs while growing in a wide range of climates. The results of my efforts were successful. The new and improved Ilex variety of the present invention was produced which can be distinguished from each of its parents and from all other forms of Ilex of which I am aware.

The new and distinct variety of *Ilex* × *meserveae* of the present invention is characterized particularly as to novelty by the unique combination of:

(a) a vigorous densely branched growth habit which assumes a pyramidal configuration,
(b) bears deep green foliage having a very glossy upper surface,
(c) bears pistillate flowers in abundance mostly during the first half of May when grown in Southern Pennsylvania,
(d) forms in profusion berries which when mature exhibit an attractive lemon-yellow coloration, and
(c) exhibits a cold tolerance substantially the same as that of *Ilex* × *meserveae* 'Blue Princess' (U.S. Plant Pat. No. 3,675).

The plants of the new variety are upright in configuration and tend to be broader at the base than at the top. The leaves have a deep satiny green appearance with good luster on the upper surface. Spines are present on the leaves (as illustrated); however, these spines tend not to snag or catch clothing to any significant degree when contact is made. The berries when mature have a coloration which is unique in Ilex plants of this class. Such berries are of a highly visible lemon-yellow coloration with occasional orange shading. The cold tolerance is greatly improved over that of its parent, *Ilex aquifolium* 'Fructa Lutea'. For instance, the new variety has overwintered well even when grown in containers above the ground at West Grove, Pa.

Most two-year-old container-grown plants of the new variety are at least as vigorous as those of the Blue Princess variety (U.S. Plant Pat. No. 3,675) and commonly measure approximately 12 to 15 inches in height and breadth when grown at West Grove, Pa. A five-year-old plant of the new variety commonly has a height of approximately 4 feet, and a twelve-year-old plant commonly has a height in excess of 8 feet.

Asexual propagation of the new variety by cuttings has been carried out at St. James, N.Y. and at West Grove, Pa. It has been confirmed that the unique combination of characteristics of the new variety has been stably established and is well transmitted to successive generations.

The new variety has been named the Mesgolg variety and is being marketed by The Conard-Pyle Company of West Grove, Pa., under the Golden Girl trademark.

BRIEF DESCRIPTION OF THE PHOTOGRAPH

The accompanying photograph of FIG. 1 illustrates typical foliage and berries of the new variety in color as true as it is reasonably possible to make the same in a color illustration of this character. This photograph was obtained during the fall of 1989 and depicts a portion of a plant of the new variety while growing at West Grove, Pa.

DETAILED DESCRIPTION

Figure 1:
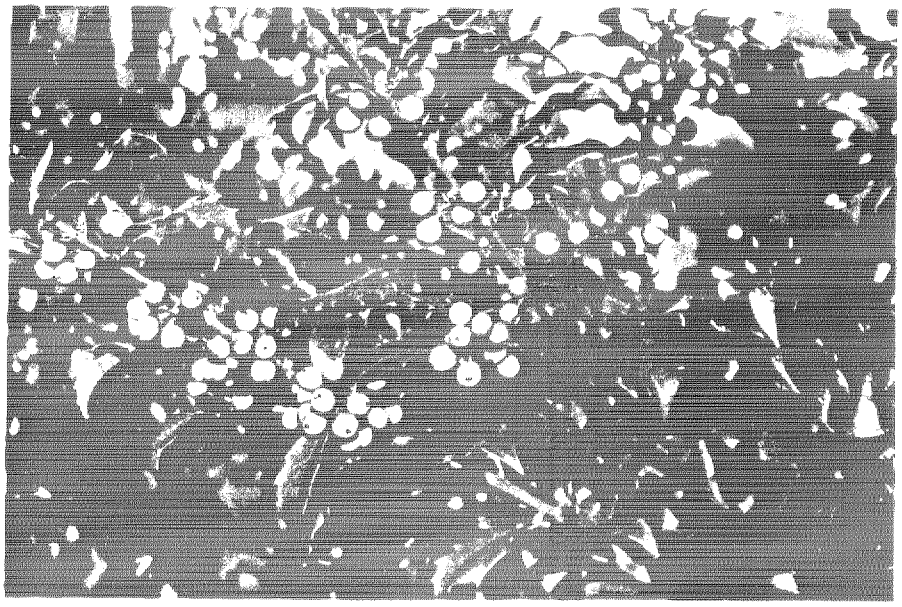

The following is a detailed description of my new variety prepared by observing twelve-year-old plants growing in the ground at West Grove, Pa. Color terminology is in accordance with the RHS Colour Chart of The Royal Horticulatural Society, London, England, except where general color terms of ordinary dictionary significance are used.

Type: Hardy outdoor evergreen shrub for garden decoration and general landscape use. Is particularly suited for growing as a specimen plant, a hedge, or a foundation plant.

Parentage: *Ilex aquifolium* 'Fructa Lutea' × Ilex rugosa.

Class: *Ilex × meserveae.*

Propagation: It does hold its distinguishing characteristics through succeeding propagations by cuttings.

Foliage:

*Type.*—Evergreen. Leaves are elliptic and curling near the tip towards the lower surface. Leaf margins are spiny with commonly approximately 8 to 12 spines on leaves appearing on lateral branches of the current year's growth, and commonly approximately 12 to 15 spines on leaves appearing along the main stem of current year's growth. There is a single spine at the apex of each leaf.

*Size.*—Mature leaves on a main stem when measuring to the tips of the spines commonly are approximately 5.5 to 7 cm. in length on average, and approximately 2.2 to 3.0 cm. in width on average.

*Petiole.*—Approximately 1 cm. in length. The upper surface is yellowish green stained with greyish red, and the under surface is light green stained with reddish coloration.

*Color.*—When observed during May, mature leaves are on the upper surface very glossy and dark green, Green Group 139A, and on the under surface are Yellow-Green Group 146A; and older leaves are Yellow-Green Group 146A on the upper surface, and Yellow-Green Group 146C on the under surface. Young stems are Yellow-Green Group 146B and mature stems are Yellow-Green Group 148A on the side facing the center of the shrub and on the outside are Yellow-Green Group 148B strongly tinted with Grey-Brown Group 199A.

Flowers: Pistillate flowers are commonly borne several to the stem in clusters of 3 to 5 on average on normal medium stems of the previous year's growth. Such flowers commonly are borne freely outdoors. The flowers are borne on a light green smooth peduncle, Yellow-Green Group 146D. Before the calyx breaks the bud size tends to be small. Such buds are short, globular and without foliaceous appendages on the surface or extending beyond the tip of the bud. As the calyx breaks, the bud is white and strongly stained with reddish-green coloration. The white blooms are approximately 0.8 cm. in diameter, and the color is White Group 155B on the upper surface and White Group 155C on the under surface. The berries are substantially round and approximately 8 to 10 mm. in diameter. The peduncle length is approximately 5 to 9 mm. on average. The berries when mature are semi-glossy and lemon-yellow in coloration, Yellow Group 12A. Old berries present on the plant commonly assume a coloration of Yellow Group 12A and are strongly tinted with Orange-Red Group 31B on the lower side of the berry. During October the berry coloration commonly is Yellow-Orange Group 15A and sometimes tinged with Orange Group 29A or Orange-Red Group 31A.

I claim:

1. A new and distinct variety of *Ilex × meserveae,* substantially as illustrated and described, characterized particularly as to novelty by the unique combination of:

(a) a vigorous densely branched growth habit which assumes a pyramidal configuration, (b) bears deep green foliage having a very glossy upper surface, (c) bears pistillate flowers in abundance mostly during the first half of May when grown in Southern Pennsylvania, (d) forms in profusion berries which when mature exhibit an attractive lemon-yellow coloration, and (e) exhibits a cold tolerance substantially the same as that of *Ilex × meserveae* Blue Princess (U.S. Plant Pat. No. 3,675).

* * * * *

PLT-247 SR
C5203 OR PP 007,652